United States Patent [19]

Alvino

[11] Patent Number: 4,944,306
[45] Date of Patent: Jul. 31, 1990

[54] SPIROMETER FOR PULMONARY MEASUREMENT

[75] Inventor: Frank J. Alvino, North Caldwell, N.J.

[73] Assignee: Healthscan, Inc., N.J.

[21] Appl. No.: 420,658

[22] Filed: Oct. 11, 1989

Related U.S. Application Data

[63] Continuation of Ser. No. 107,878, Oct. 13, 1987, abandoned, which is a continuation of Ser. No. 912,642, Sep. 29, 1986, abandoned, which is a continuation of Ser. No. 715,563, Mar. 25, 1985, abandoned.

[51] Int. Cl.$^5$ .............................................. A61B 5/08
[52] U.S. Cl. ................................................. 128/725
[58] Field of Search ..................... 128/716, 725, 727

[56] References Cited

U.S. PATENT DOCUMENTS

| 471,389 | 3/1892 | Lacey | 128/725 |
|---|---|---|---|
| 2,292,474 | 8/1942 | Paxton | 128/716 |
| 3,871,364 | 3/1975 | Boehringer | 128/727 |
| 3,958,565 | 5/1976 | Wright | 128/727 |
| 4,041,935 | 8/1977 | Garbe | 128/727 |
| 4,158,360 | 6/1979 | Adams | 128/725 |
| 4,284,083 | 8/1981 | Lester | 128/727 |
| 4,403,616 | 9/1983 | King | 128/725 |

FOREIGN PATENT DOCUMENTS 1160669 8/1969 United Kingdom .

Primary Examiner—William E. Kamm
Attorney, Agent, or Firm—Wolder, Gross & Bondell

[57] ABSTRACT

An improved spirometer to indicate peak flow expiration from a patient, as well as to enhance pulmonary monitoring. Perpendicular to the standard mouthpiece is a chamber with a centrally positioned rod guiding a spring biased piston, responsive to expiration-induced air flow from the patient.

1 Claim, 3 Drawing Sheets

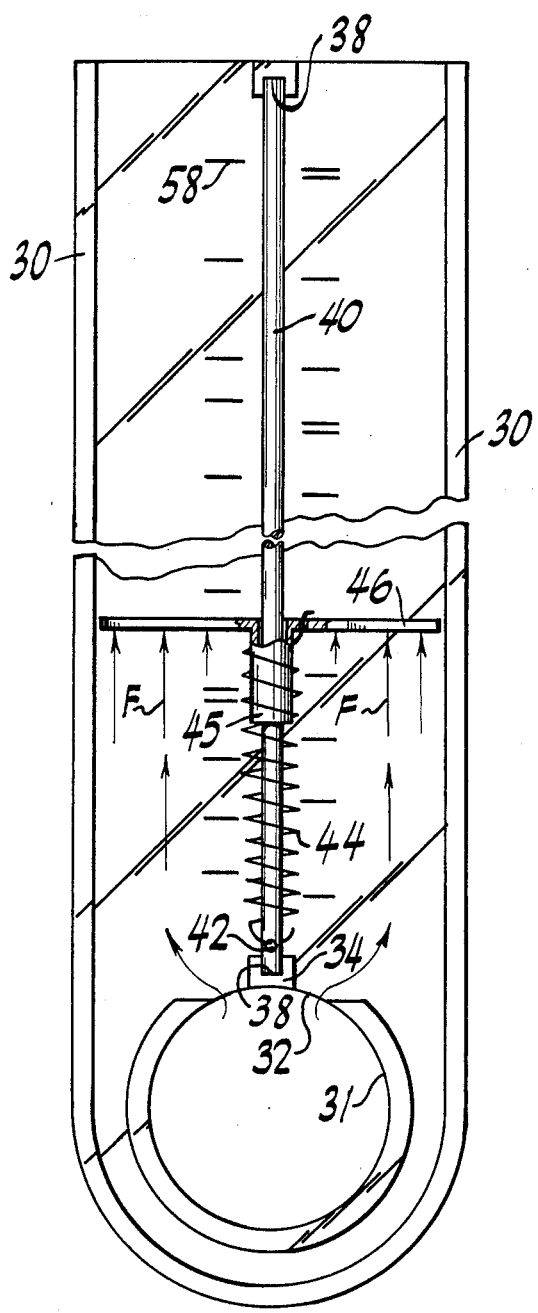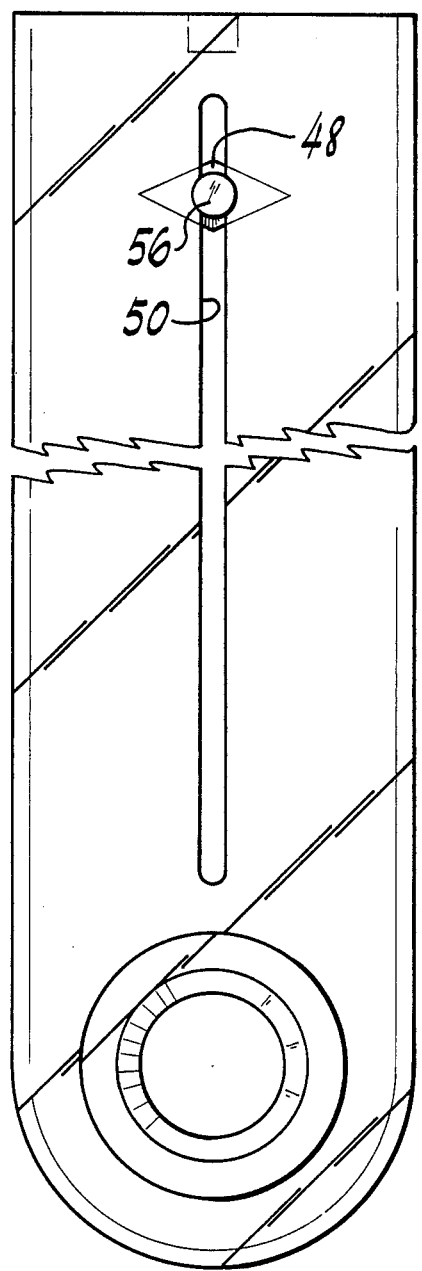
FIG. 3
FIG. 5

SPIROMETER FOR PULMONARY MEASUREMENT

This application is a continuation of application Ser. No. 107,878, filed 10/13/87, now abandoned, which is a continuation of Ser. No. 912,642, filed 9/29/86, now abandoned, which is a continuation of Ser. No. 715,563, filed Mar. 25, 1985, now abandoned.

BACKGROUND OF THE INVENTION

The present invention relates generally to expiration flow rate measuring and monitoring devices, and more particularly to devices which are significantly simplified and improved over prior art units.

It has been found that the measure of peak expiratory flow rate is a good general indicator of the presence or absence of airways obstruction within the body. Thus such a device is useful in measuring the degree of response of the patient to bronchodilators. This is particularly helpful since obstruction of the airways usually associated with-lung disease, is measurable long before any other symptoms may appear. The measurement or the indication of a change in peak expiratory flow rate is an effective medical tool especially if screening techniques can be accomplished away from hospital or medical office environments, such as homes, places of business, etc.

Such a self administered test by the patient, who then could be in communication with his or her physician, could indicate the severity of an asthmatic attack, for example.

U.S. Pat. No. 4,158,360 is an excellent example of the prior art and the provision of such a device has in the past met the parameters required to accomplish the above ends. However, this device utilizes a central channel in an otherwise perpendicular upright member with a floating ball and a pin to position the ball at specific locations. The orifice opening may be restricted by a disc having varying diameter openings within its central face in order to vary the effect of the flow rate from the patient. This construction, while proving substantially acceptable, does not provide for simplicity of operation and preciseness in the measurement of the flow rate, since it requires the user to set or adjust the position of the ball prior to use.

U.S. Pat. No. 471,389 indicates an early construction of a spirometer utilizing a piston G biased by a spring K. It is obvious that the construction is more involved and does not allow for the accuracy present in the subject invention.

Another example of the prior art is British Patent No. 1,160,669 which discloses a spring loaded piston operating in the same direction as the flow of air from the patient. Once again, this construction is more involved than that of the subject invention, and does not provide the simplicity of construction and the accuracy of flow rate indication of the present invention.

Accordingly, among the principal objects of the present invention is to provide an improved spirometer.

Still yet a further object of the present invention is to provide a spirometer having spring biased piston mechanism to accurately indicate the peak flow rate of the patient as well as to assist in training to meet specific goals.

Still yet another object of the present invention is to provide a spirometer of the character described which will be simple and inexpensive to manufacture and yet will be durable to a high degree in use.

BRIEF DESCRIPTION OF THE INVENTION

The present invention is directed to an improved spirometer in which the indicating chamber is substantially hollow and has positioned therein along its major axis a rod carrying a piston which is biased by an extension spring secured to the base of the rod. The rod is positioned directly along a perpendicular radius from the central axis of the mouthpiece. There are openings to allow air to pass from the mouthpiece perpendicular to the chamber to inpinge directly upon the lower surface of the piston. Depending upon the flow rate that can be created by the patient, the piston will move upwardly, the length of movement to be indicated along a scale which may be calibrated as desired. The mouthpiece may have an orifice extension on the other side of the chamber from the mouthpiece, and optionally the orifice may be provided with a rotatable disc to vary the diameter opening of the orifice.

An indicator is movably positioned either by force from the piston or by manual movement of an archoring post riding in a vertical slot.

The above description, as well as further objects and advantages of the present invention will be more fully appreciated with reference to the following detailed description of a preferred, but nonetheless illustrative embodiment of the invention, when taken in conjunction with the following drawings, wherein:

FIG. 3 is a cross-sectional view taken along the lines 3—3 of FIG. 2; and

FIG. 5 is an elevational break view of FIG. 2.

DETAILED DESCRIPTION OF THE INVENTION

Figure 1:
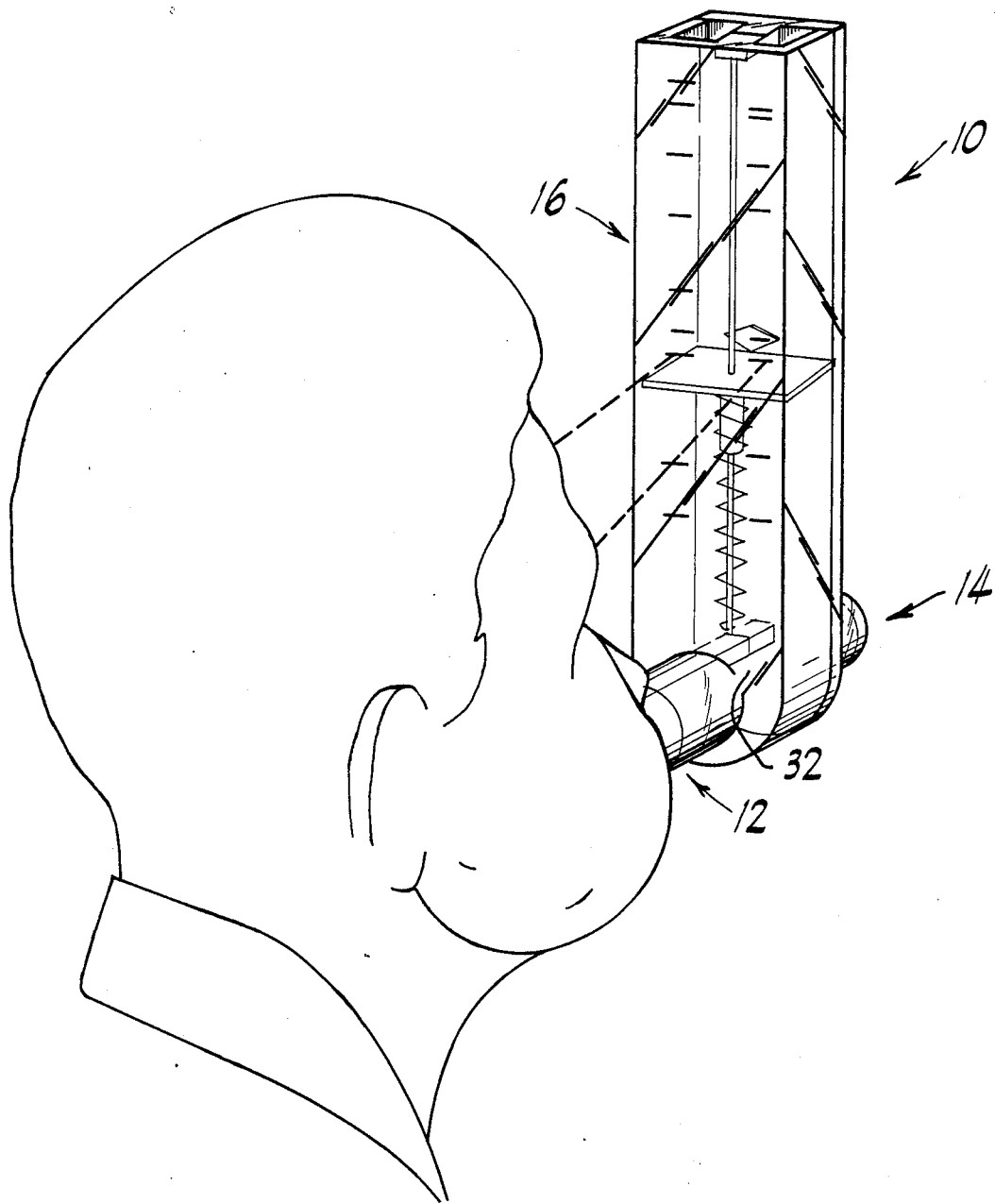
FIG. 1 is an upper rear prospective view showing the patient utilizing the improved spirometer while viewing the indicator carried by the piston.
Figure 4:
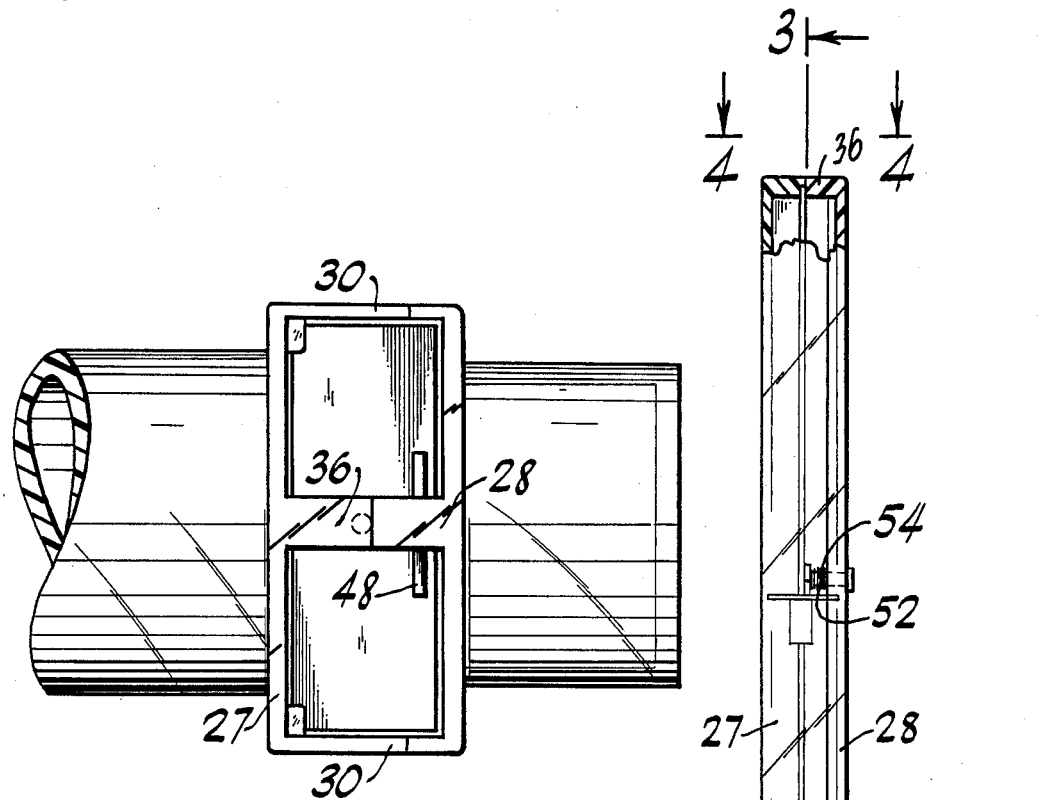
FIG. 4 is a cross-sectional view taken along the lines 4—4 of FIG. 2.

Turning in detail to the drawings, and more particularly to FIG. 1, there is shown an improved spirometer 10 broadly comprising a mouthpiece 12, an orifice extension 14 and an upright chamber 16. The meter may be constructed of any suitable plastic or glass.

Figure 2:
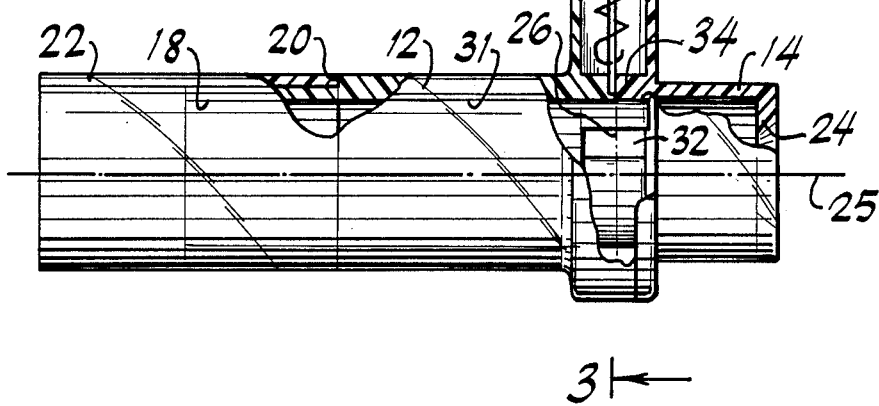
FIG. 2 is an enlarged, partly cut away, side elevational view showing details of the construction.

Turning to FIG. 2, the mouthpiece 12 is defined by an opening 18 on the exterior terminating in a step shoulder 20. This is to receive the mouthpiece cover 22 which may be made of paper or plastic so that it is disposable or may be easily removed and cleaned.

The orifice extension 14 has a orifice opening 24 of decreased diameter allowing complete axial communication between the opening of the mouthpiece cover and mouthpiece and the orifice. The units together form a cylindrical member with air passing along the major axis 25 which is coincident with the axes of the mouthpiece and the orifice extension. There are means to vary the opening of the orifice extension 24, such as disc carrying central openings of varying diameters. This is known in the art, and is well illustrated in U.S. Pat. No. 4,158,360, and is not otherwise illustrated in the present drawings.

The chamber 16 is positioned between the mouthpiece and the orifice extension and has a central axis 26 which is perpendicular to the central axis 25 and extends radially therefrom. The securement may be made by means of molding the unit with as a single piece with the front wall 27 and the back wall 28 of the chamber being molded to the side wall formed of the mouthpiece and the orifice extension. The chamber is further defined by side walls 30. The inner wall 31 of the cylindrical mouthpiece/extrusion unit has defined therein air passages 32 to allow movement of expirated air into the chamber 16. Positioned centrally over the chamber is a lower bridge 34 at the base of the chamber and which is opposed oppositely an upper bridge 36 at the top of the chamber. The bridges each have receptacles 38 to anchor the rod 40 (FIG. 3) which lies along the central axis 26. At its base, the rod has a horizontal bore 42 which receives the lower end of an extension compression biased spring 44, the upper end of which is secured to an enlarged diameter anchoring portion 45 of a piston 46. An indicator 48 is slidably secured in vertical slot 50 by compression spring 52 surrounding rod 54 which extends outside the chamber 16 which terminates in an enlarged head 56. Positioned on the outer sides of the chamber, most conveniently on the front wall 27 is a scale 58.

In operation, the patient places a mouthpiece cover 22 over the mouthpiece adjusts the orifice opening, as desired and then proceeds to blow into the mouthpiece. A portion of the air passing through the mouthpiece will move perpendicular through the air passages 32 and inpinge on the lower surface of the piston with a force F. This will cause the piston to move against the force stored in the extension biased spring 44. Depending on the force, the piston will be moved up a certain distance within the chamber. The calibration of this distance may be indicated by the viewer noting the position of the indicator 48 along the scale 58, as best seen in FIG. 1. The scale is calibrated to compensate for the air flowing out of the vertical slot 50.

Because of the resistance spring, it is not necessary to utilize varying scales, with significantly varying orifices, although a set of varying orifices for the orifice extension, may be provided if desired. Furthermore, the user may rapidly and readily note the indicator position along the scale or adjust it to act at a target goal. Furthermore, there can be more than one scale on the front wall of the chamber so as to indicate varying levels of flow. Should there be provided means to vary the diameter of the orifice extension. Accordingly, the additional structure and the ambiguity of the measurements that were present in the '360 patent are overcome in the present construction making for a unit that is simplier to manufacture, assemble and operate, and yet is more precise in the measurements that may be required from it. This device may easily be used outside of a hospital or medical office environment, and is subject to abuse and other rough treatment without loosing its efficacy.

As can be seen, the present invention constitutes a significant advance over the state of the technology. As numerous additions, modifications and constructions can be performed within the scope of the invention, such scope is to be measured by the claims herein.

What is claimed is:

1. A spirometer comprising a vertically-oriented chamber having opposed front and back walls, an open top formed as a pair of exit passageways divided by an upper central bridge element between said front and back walls, and an open bottom formed as a pair of entrance passageways divided by a lower central bridge element between said front and rear walls; a hollow inlet member mounted to and projecting outwardly from said front wall at the lower end thereof; a hollow outlet member mounted to and projecting outwardly from said back wall at the lower end thereof, said outlet member including an outlet orifice of reduced diameter at the distal end thereof, the interior of said inlet and outlet members being joined to the interior of said chamber through said entrance passageways to allow the passage of air therethrough; a piston mounted in said chamber for vertical movement therein; a guide rod centrally mounted within said chamber, the opposed ends thereof being supported by said upper and lower central bridge elements, said piston having a vertical central throughbore whereby said piston is mounted on said guide rod; spring means mounted to said piston to urge said piston to a lower retracted position, said piston being movable upward along said guide rod in response to a flow of air through said inlet member into said chamber; an indicator mounted within said chamber for upward movement with said piston; a vertical slot located in a wall of said chamber; a shank extending from said indicator through said vertical slot and terminating in an enlarged head externally of said chamber; and a helical compression spring encircling said shank and entrapped between said indicator element and the inside face of said chamber bordering said slot.

* * * * *